(12) United States Patent
Musbach et al.

(10) Patent No.: US 6,736,841 B2
(45) Date of Patent: May 18, 2004

(54) TEXTURED AND/OR MARKED BALLOON FOR STENT DELIVERY

(75) Inventors: Frank Musbach, St. Paul, MN (US); Kent James Zachman, Buffalo, MN (US); Tracee Eidenschink, Wayzata, MN (US); Wang Leng Yang, Minneapolis, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/209,796

(22) Filed: Jul. 31, 2002

(65) Prior Publication Data

US 2003/0004535 A1 Jan. 2, 2003

Related U.S. Application Data

(62) Division of application No. 09/283,367, filed on Mar. 31, 1999.

(51) Int. Cl.7 .................................................. A61F 2/06
(52) U.S. Cl. ............... 623/1.11; 604/103.1; 604/103.08
(58) Field of Search ........................ 604/103.08, 103.01, 604/103.07, 103.1; 623/1.11

(56) References Cited

U.S. PATENT DOCUMENTS

| 2,927,584 A | 3/1960 | Wallace ................ 604/103.08 |
| 4,927,412 A | 5/1990 | Menasche |
| 5,074,845 A | 12/1991 | Miraki et al. |
| 5,250,070 A | 10/1993 | Parodi |
| 5,397,307 A | 3/1995 | Goodin |
| 5,423,745 A | 6/1995 | Todd et al. |
| 5,456,666 A | 10/1995 | Campbell et al. |
| 5,478,319 A | 12/1995 | Campbell et al. |
| 5,487,730 A | 1/1996 | Marcadis et al. |
| 5,545,132 A | 8/1996 | Fagan et al. |
| 5,653,690 A | 8/1997 | Booth et al. |
| 5,693,014 A | 12/1997 | Abele et al. |
| 5,746,745 A | 5/1998 | Abele et al. |
| 5,772,669 A | 6/1998 | Vrba |
| 5,776,141 A | * 7/1998 | Klein et al. ................. 623/1.11 |
| 5,826,588 A | 10/1998 | Forman |
| 5,836,895 A | 11/1998 | Ramsey |
| 5,989,230 A | * 11/1999 | Frassica ...................... 604/264 |
| 6,048,332 A | 4/2000 | Duffy et al. ................. 604/104 |
| 6,264,631 B1 | 7/2001 | Willis et al. ........... 604/103.08 |

FOREIGN PATENT DOCUMENTS

| WO | 94/23787 | 10/1994 |
| WO | 98/07390 | 2/1998 |

OTHER PUBLICATIONS

U.S. patent application Ser. No. 09/283367, filed Mar. 31, 1999.

* cited by examiner

*Primary Examiner*—Brian L. Casler
*Assistant Examiner*—Jeremy Thissell
(74) *Attorney, Agent, or Firm*—Vidas, Arrett & Steinkraus, P.A.

(57) ABSTRACT

Desired portions of a balloon may be marked by varying the texture of the surface. Marking the balloon facilitates positioning of the balloon on a catheter and facilitates positioning a medical device on the balloon.

3 Claims, 4 Drawing Sheets

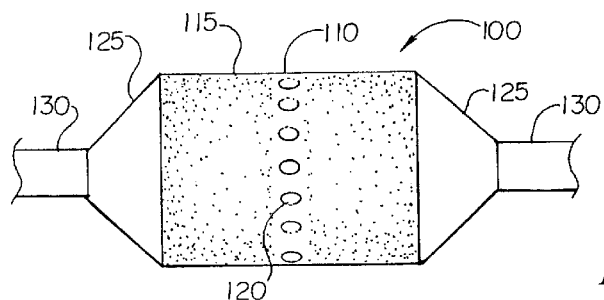
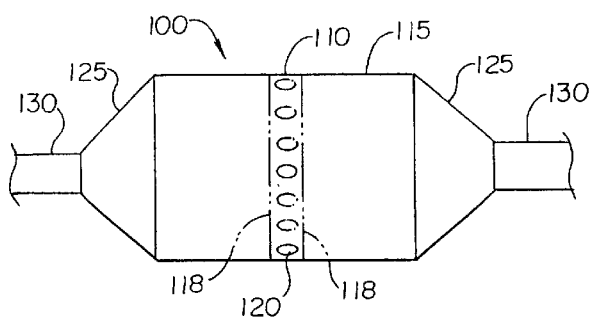
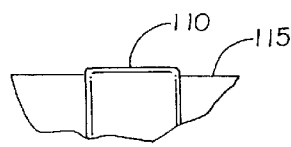
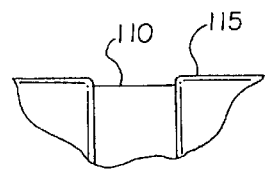
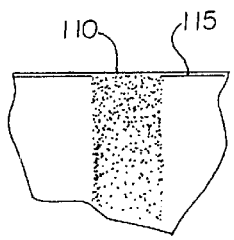
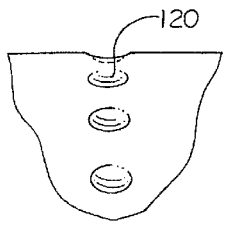
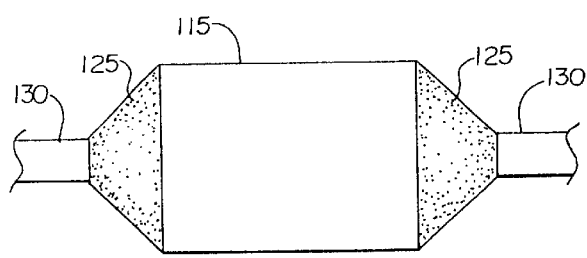
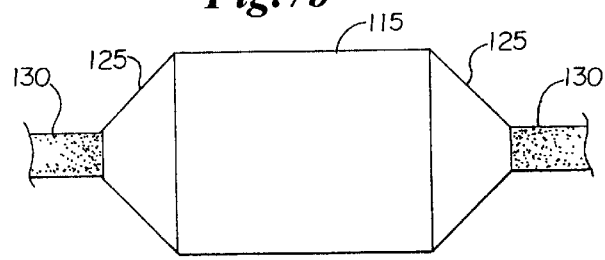

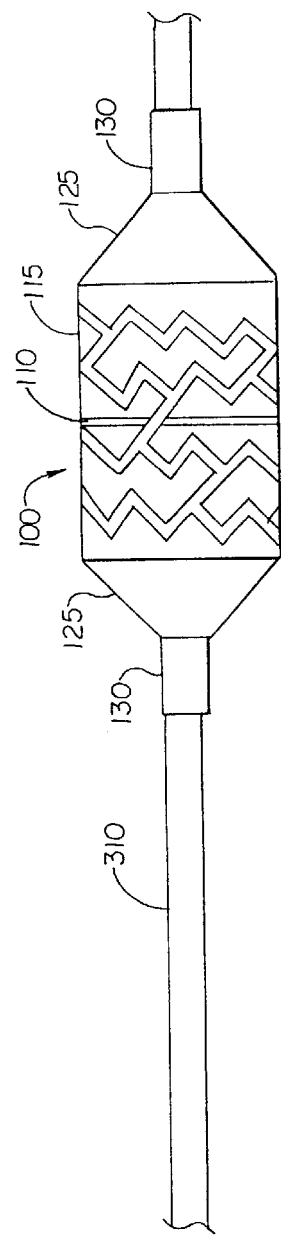
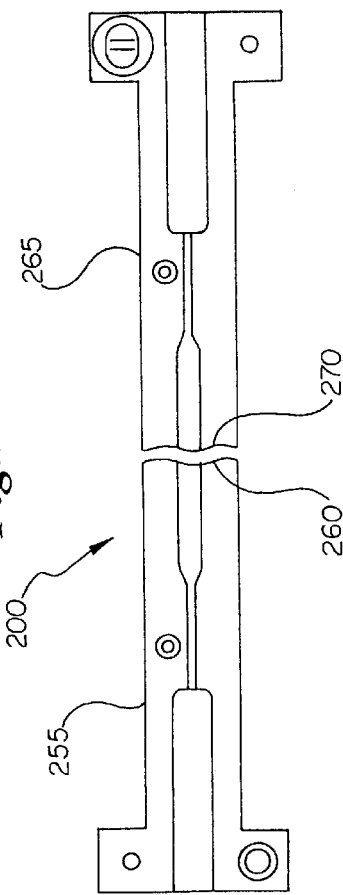
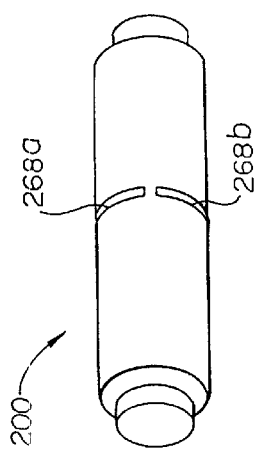

TEXTURED AND/OR MARKED BALLOON FOR STENT DELIVERY

CROSS-REFERENCE TO RELATED APPLICATIONS

This Application is a Divisional Application claiming priority to copending U.S. application Ser. No. 09/283,367 filed Mar. 31, 1999, the entire contents of which are incorporated herein by reference.

BACKGROUND OF THE INVENTION

The use of a medical balloon for delivery of an expandable, implantable medical device such as a stent, stent-graft, graft or vena cava filter to a desired bodily location is well known in the art. Typically, an expandable, implantable medical device such as a stent is disposed about a balloon which in turn is mounted on a catheter tube. The catheter is inserted into a bodily vessel and advanced to a desired location. The balloon is then inflated so as to expand or assist in expanding the medical device.

In balloon expansion of an expandable, implantable medical device, it is important that the medical device be accurately positioned on the body portion of a balloon. Failure to properly position the medical device on the balloon may result in a non-uniform expansion of the medical device. If a portion of the medical device extends over the cone or waist portions of the balloon, for example, that portion of the medical device may not be fully expanded by the balloon.

Unfortunately, the proper positioning of such a medical device on a balloon can be a challenging task because the medical device is typically mounted on an uninflated balloon. In the uninflated state of the balloon, it is difficult to discern where the proximal and distal cones end and where the body portion of the balloon begins It is also important to properly position the balloon itself on the catheter so that the various portions of the balloon are disposed in desired locations along the catheter and are properly aligned. Again, this task can be challenging because the balloon is necessarily in the uninflated state when mounted on a catheter thereby making it difficult to distinguish between the various portions of the balloon. The problem is exacerbated when dealing with an uninflated, foldable balloon.

The tolerance errors associated with the production of balloons and the mounting of a balloon on a catheter and in mounting the stent to the balloon can compound leading to a stacking of tolerance errors. The tolerance errors are increased when the balloon is positioned relative to marker bands that have been mounted on the catheter.

To that end, there is a need for improved methods of positioning a balloon on a catheter, for positioning an expandable, implantable medical device on a balloon and for maintaining the positioning of the device once it is on the balloon.

There is also a need for balloons whose various portions may be readily identified even in the uninflated state of the balloon to facilitate mounting of the balloon on a catheter and/or mounting a medical device thereon.

For the purpose of this disclosure, the term expandable, implantable medical device shall refer to stents, grafts, stent-grafts and vena cava filters, whether self-expandable, balloon expandable or otherwise expandable.

All U.S. patents and all other published documents mentioned anywhere in this application are incorporated herein by reference in their entirety.

BRIEF SUMMARY OF THE INVENTION

The present invention relates to medical balloons with a textured, partially textured or otherwise marked surface. The texturing or marking facilitates the positioning of an expandable, implantable medical device on the balloon and increases the securement of a stent or other expandable, implantable medical device to the balloon.

In one embodiment, the inventive balloons are marked via a variation in the opacity of the balloon material in the regions to be marked.

In another embodiment, the inventive balloons are marked via one or more protrusions or dimples in the desired region of the balloon.

In yet another embodiment, the inventive balloons are marked by a different texture in the marked region.

The invention contemplates marking the balloons in at least one of several desired regions in particular. These desired regions include the center of the balloon and the proximal and distal cone/body interfaces.

The invention is also directed to methods of positioning a balloon on a catheter and to methods of positioning a stent or other medical device on a balloon using the inventive marked balloons.

BRIEF DESCRIPTION OF THE SEVERAL VIEWS OF THE DRAWING(S)

FIG. 1 shows a fragmentary side elevational view of an inventive balloon;

FIG. 2 shows a fragmentary side elevational view of an inventive balloon;

FIG. 3 shows a fragmentary side elevational view of an inventive balloon;

FIG. 4 shows a fragmentary side elevational view of an inventive balloon;

FIG. 5 shows a fragmentary side elevational view of an inventive balloon;

FIG. 6 shows a fragmentary side elevational view of an inventive balloon;

FIG. 7a shows a fragmentary side elevational view of an inventive balloon;

FIG. 7b shows a fragmentary side elevational view of an inventive balloon;

FIG. 8 shows a side elevational view of an inventive balloon and stent mounted on a catheter;

FIG. 9a shows a mold which may be used in forming the balloons of the present invention;

FIG. 9b shows another mold which may be used in forming the balloons of the present invention;

DETAILED DESCRIPTION OF THE INVENTION

Figure 10:
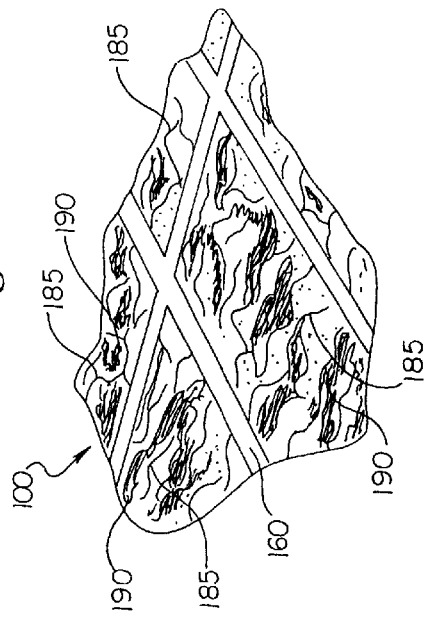
FIG. 10 is a fragmentary perspective view of a stent mounted on an inventive balloon.

While this invention may be embodied in many different forms, there are described in detail herein specific preferred embodiments of the invention. This description is an exemplification of the principles of the invention and is not intended to limit the invention to the particular embodiments illustrated.

The present invention is directed to medical balloons that have textured or otherwise marked surfaces. These textured or otherwise marked balloon surfaces facilitate positioning of the balloon on a catheter and/or positioning an expandable, implantable medical device about the balloon.

The invention contemplates several specific regions of the balloon to be marked. These regions include the center portion of the balloon, the body portion of the balloon, the body-cone interfaces the proximal and distal cones and the proximal and distal waists.

One embodiment of the invention, as shown in FIG. 1, consists of a medical balloon shown generally at 100, whose body portion 115 is marked with a textured surface. The middle portion of the balloon is marked with a band 110 traversing the circumference of the balloon. Band 110 consists of a series of bumps 120 extending outward from the surface of the balloon. Band 110 has a non-textured surface to aid in distinguishing it from the remainder of body portion 115. Alternatively, band 110 may be textured identically to the remainder of the body portion with only the bumps 120 and marker lines 118 serving to highlight the middle of the balloon as shown in FIG. 2. Band 110 may also be a slightly raised surface, as shown in FIG. 3 or a slightly indented surface, as shown in FIG. 4. Band 110 may also be textured differently from the surrounding surface of the balloon as shown in FIG. 5. Desirably, the difference in texture between band 110 and adjacent regions 115 will be visible, as shown in FIG. 5. The texturing of band 110 and the surrounding body portion 115 may be reversed so that band 110 is untextured and surrounding body portion 115 is textured. Desirably, band 110 will have a width of from about 0.005 inches to about 0.015 inches. More desirably, the width of the band will be from about 0.005 inches to about 0.008 inches. Narrow bands which are visible under a microscope may also be used. Wider bands may be used as well. Band 110 need not be continuous around the circumference but may have interruptions therein.

The combination of a textured body portion 115 and non-textured cone portions 125, as shown in FIG. 1 further allows for easy identification of the interface between body portion 115 and cone portions 125. The middle of the balloon may also be marked by the optional presence of dimples 120 as in FIG. 6.

The invention also contemplates providing a non-textured body portion 115 as shown in FIG. 7a in conjunction with textured or otherwise marked cone portions 125. Alternatively, body portion 115 may be textured differently from cone portions 125. The difference in texture between the body and cone portions serves to highlight the junction between the body and cone portions. The embodiment of FIG. 7a may also be provided with a marking to show the middle of the balloon.

In another embodiment, as shown in FIG. 7b, a medical balloon shown generally at 100, is provided with marked waist sections 130. Adjacent cone portions may be untextured or may have a texture differing from adjacent cone portions 125 so as to highlight the junction between the cone and waist portions as well as between the cone and body portions.

FIG. 8 shows a balloon 100 with marked band 110 traversing the circumference of the balloon in the middle. Balloon 100 is disposed about catheter tube 310. Stent 160 is disposed about balloon 100, having been aligned using band 110.

Desirably, the texturing, consisting of a series of peaks and valleys, will have a depth of about 0.0005 inches to about 0.001 inches as measured from peak to valley. Deeper or shallower texturing may also be employed. Also desirably, the peak to peak distances will be at least about 0.005 inches. Textures with smaller peak to peak distances may also be employed.

The invention also contemplates balloons in which only one of the proximal or distal cone and/or waist portions is marked. The invention further contemplates balloons in which the center is marked, as in FIG. 1, along with at least one of the proximal or distal cone and/or waist portions as in FIGS. 7a and 7b.

A number of different techniques may be employed to mark or texturize the desired portions of the balloon. One suitable technique involves using a textured mold during the molding of the balloon. Desired portions of the mold may be textured by bead blasting, etching or electric discharge machining. The texture of the mold is then transferred to the balloon during the molding.

Marker lines may be provided on a balloon by using a split mold as shown in FIG. 9a. The mold, shown generally at 200 includes a first half 255 and a second half 265. First half 255 and second half 265 are provided with edges 260 and 270, respectively. On molding a balloon, an image of the edge will be marked on the balloon surface. The edges of the split mold may be beveled to accentuate the marker line.

Another suitable mold is shown generally at 200 in FIG. 9b. Mold 200 has two notches 268a,b cut therethrough. Each of the notches extends all the way through the mold.

The inventive balloons may be made by incorporating the textured surface into the balloon via a mold heat set process using molds such as those shown above. Prior to molding, the balloon may be pre-blown using a standard commercial process. The balloon may also be stretched prior to molding, desirably in a separate step. The stretching may also be combined with a blowing step. More generally the balloon may be subject to any of the standard processes for treating a balloon between extrusion and molding. Once in the mold, the balloon preform is heated to a desired temperature so as to incorporate the texturing into the balloon. The particular temperature will depend on the choice of balloon material. During the molding, the balloons are blown. One suitable molding process is set out in greater detail in U.S. Pat. Nos. 5,456,666 and 5,478,319.

Other techniques for forming markings on the surface of the balloon or texturizing the balloon include selective removal of materials from a balloon preform or a balloon such as laser ablation, etching, grinding or other techniques as disclosed in U.S. Pat. No. 5,826,588 to Forman.

In one embodiment of the invention the marked surface consists of a roughened area of the balloon. It is desirable that the roughening be visible. With appropriate balloon materials and an appropriate amount of roughening, the opacity of the marked area will differ from that of surrounding regions.

The balloon may also be marked by applying a marking compound such as an ink, die or other suitable colored, fluorescent or ultraviolet absorbing compound, thereto. Suitably, the marking compound will be biocompatable. Desirably, the marking compound will be applied to the textured or roughened surface.

The invention also contemplates applying a marking compound to the interior of the balloon. The marking compound should be visible through the balloon. The interior surface of the balloon may optionally be roughened or otherwise textured as well.

The texturing or other marking disclosed herein may be provided on any suitable balloon intended for use in delivering a medical device mounted thereabout. As such, the physical characteristics of the balloon may vary. The balloon may be compliant or non-compliant or may be compliant in-part and non-compliant in part. The wall thickness of the balloon may be constant over the entire balloon or may vary in different parts of the balloon. The balloon may be formed of one layer of material or may consist of a plurality of layers. The balloon may be formed of a single piece of balloon material or may be formed of several pieces joined together along the length of the balloon.

The inventive balloons may be made from any balloon material known in the art such as polyethylene, polyethylene terephthalate (PET) including non-compliant PET, Arnitel, Hytrel, polyetherether ketone (PEEK), Pebax (all grades), Teflon as well as other polyolefins. More generally, any thermoplastic elastomer treatable by a blow molding process may be used.

The texturized balloons of the present invention provide a further advantage in improving stent tensile—i.e. increasing the force necessary to remove a crimped stent from a balloon. First, by texturizing or roughening the surface, a pattern of peaks and valleys may be formed that can better grip a stent as compared to a smooth surface. Second, where a slip coat is provided on the balloon, the slip coat can pool in the pockets, crevices, craters and other surface indentations in the roughened surface and away from the stent thereby leaving a clean, non-lubricated interface between the stent and the balloon. In order to achieve this benefit, the size of the texturing must be sufficient so as to allow for the formation of adequate areas in which the slip coat may collect. This is illustrated in FIG. 10. A balloon, shown generally at 100 has a roughened surface comprising peaks 185 and fluid-containing valleys or pools 190. Stent 160 rests on the roughened surface of balloon 100 above the pools of fluid.

In the non-textured or non-roughened portions of a balloon, the slip coat will remain on the surface of the balloon. Thus, where socks are placed over the proximal and distal ends of the balloon, it is desirable for the portions of the balloon which contact the socks to not be texturized or roughened so that the slip coat will contact the socks and facilitate removal of the socks from the balloon.

The invention is also directed to a catheter having an inventive balloon mounted thereon. Any suitable balloon-based stent delivery catheter may be used. One such catheter is shown generally at 300 in FIGS. 11 and 12. An inventive balloon 100 is disposed about an inner tube 310. The proximal end of balloon 100 is mounted to tube 330. The distal end of balloon 100 is mounted to inner tube 310. Disposed about balloon 100 is a self-expanding stent 160 which is crimped onto the catheter and held in its place with mounting bodies 372. The stent is further held in place by two overlying retaining sleeves 374. Balloon 100 is supplied with an inflation fluid by inflation lumen 320 contained in the catheter shaft such as the space between tube 310 and tube 330. The invention also contemplates the possibility of a separate tube serving as an inflation lumen. Marker bands 370 may also be included on the catheter.

Additional details about the catheter, as well as other suitable catheters for use in the present invention are disclosed in WO 98/07390.

Figure 11:
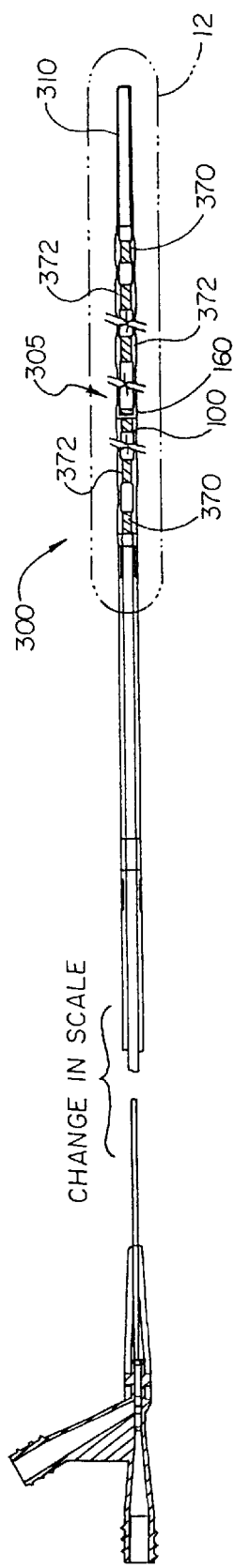
FIG. 11 shows a stent delivery catheter.
Figure 12:
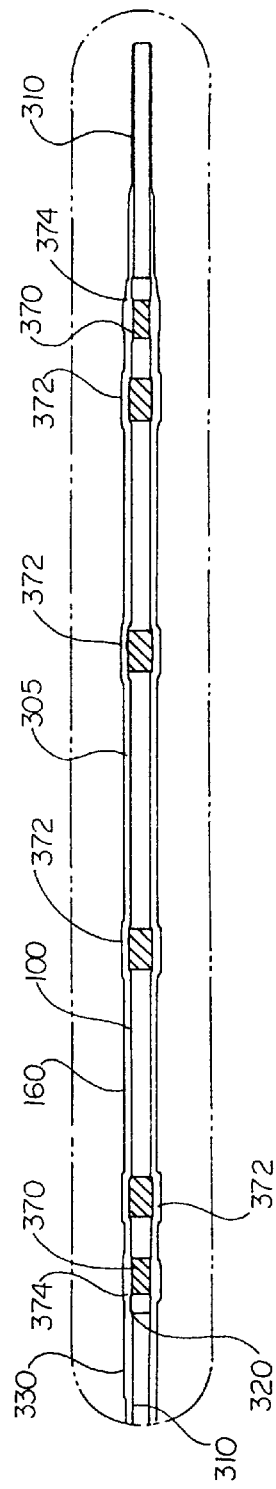
FIG. 12 shows an enlarged view of the distal end of the catheter of FIG. 11.

In addition to the over-the-wire catheter shown in FIGS. 11 and 12, the invention may be practiced with any other suitable catheter including rapid-exchange catheters and fixed wire catheters. The exact configuration of the delivery apparatus will depend on what other functions are desired.

The device of FIGS. 11 and 12 is shown with a self-expanding stent. Balloon expandable stents may also be used. Those of ordinary skill in the art will recognize any modifications necessary to the stent delivery catheter of FIGS. 11 and 12 to accommodate balloon expandable stents, stent-grafts, grafts and vena cava filters. Any other suitable device having a balloon thereon for delivery of any of the above expandable, implantable medical devices may also be used.

Figure 13:
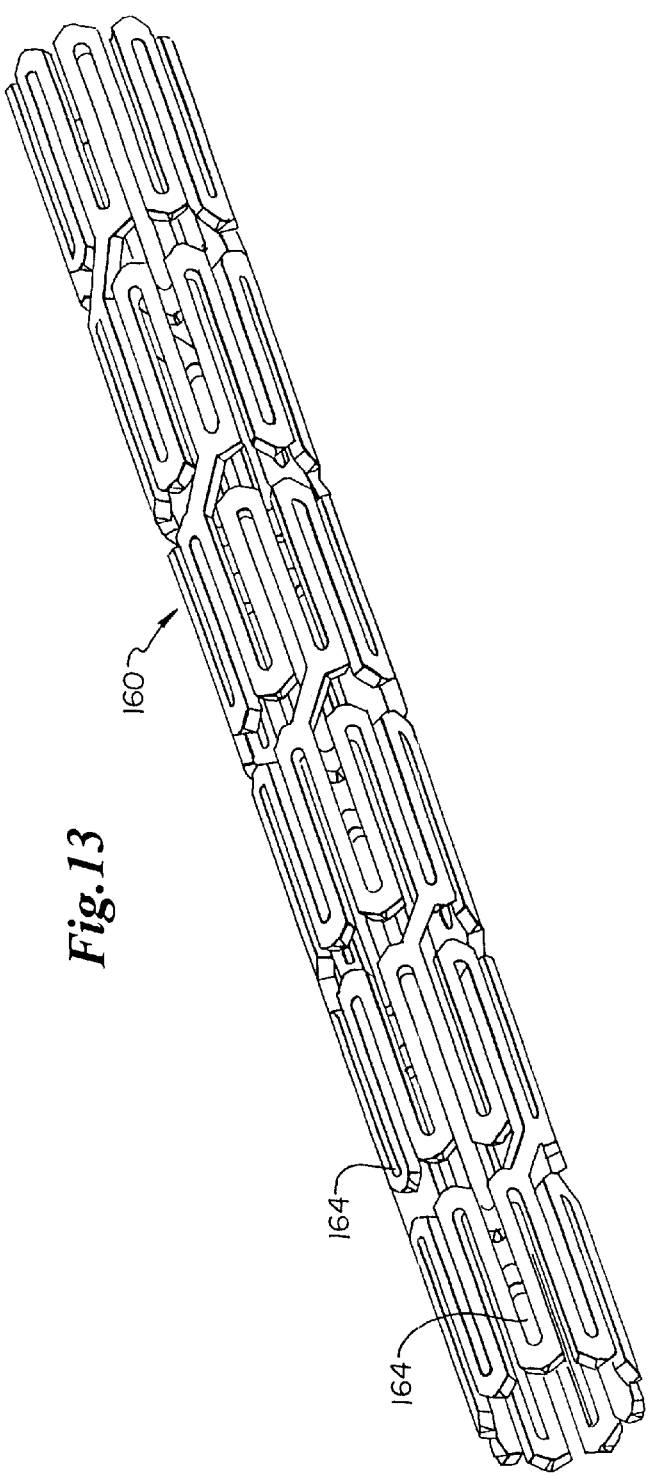
FIG. 13 shows a stent suitable for use with the present invention.

A suitable stent for use with the inventive balloons is shown at 160 in FIG. 13 for illustrative purposes. Stent 160 is formed of a plurality of interconnected struts 164. Stents with other designs may also be used in conjunction with the inventive balloons.

The invention is also directed to methods of positioning a balloon on a catheter as well as methods of positioning an expandable, implantable medical device on a medical balloon.

In particular the invention is directed to a method of positioning a balloon on a catheter which comprises the steps of providing a medical balloon with at least one position marker thereon and providing a catheter for mounting the balloon thereon. The at least one position marker is aligned with a desired portion of the catheter such as a marker band so as to position the balloon at a desired location along the catheter. Desirably, the middle of the balloon, as indicated by a suitable marking on the balloon, will be positioned with the marker band or other position indicator on the catheter. Once properly positioned, the balloon is bonded to the catheter through any suitable bonding process known in the art including the use of adhesives and heat bonding. The bonding may be commenced after the balloon has been fully aligned or as the balloon is being aligned. Any of the above disclosed balloons may be so aligned.

In another aspect, the invention is directed to a method of aligning and/or positioning an expandable, implantable medical device on a medical balloon disposed about a catheter. The method comprises the steps of providing a catheter with an inventive marked medical balloon disposed thereabout and providing an expandable, implantable medical device for disposing about the balloon. The expandable, implantable medical device is disposed about the balloon and positioned in a desired position about the balloon using the one or more markers on the balloons as a positioning guide.

Although the inventive method specifically contemplates positioning stents (including balloon expandable and balloon assisted), stent grafts, grafts and vena cava filters, the method may also be applied more broadly to any other medical device that may be delivered via a catheter and is disposed about a balloon.

To that end, the present invention provides for the marking of a medical balloon to facilitate both the positioning of the balloon on a catheter as well as the positioning of a medical device mounted about the balloon.

In another aspect, the invention is directed to methods of using the inventive medical balloon and in particular to a method of delivering an expandable, implantable medical device such as a stent to a bodily location using the inventive balloon. A medical device delivery apparatus comprising an inventive balloon mounted on a catheter is provided. The balloon has been positioned on the catheter using the markings thereon and desirably using a marking indicating the middle of the balloon. The balloon is in fluid communication with an inflation lumen which is capable of supplying an inflation fluid to the balloon.

At least a portion of the apparatus, including the balloon and expandable, implantable medical device is inserted in a bodily vessel and advanced to a desired bodily location. The balloon is inflated so as to expand and/or seat and/or deploy the expandable, implantable medical device. The balloon is then at least partially deflated such that it no longer engages the expandable, implantable medical device. The apparatus is then withdrawn from the body, having deployed the expandable, implantable medical device.

The above disclosure is intended to be illustrative and not exhaustive. This description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

We claim:

1. A method comprising the steps of:

providing a medical balloon, having an external surface, a first end, a second end and a middle portion positioned midway between the first end and second end with at least one position marker thereon to indicate the position of the middle portion, the at least one position marker comprising a textured portion of the external surface;

providing a catheter for mounting the balloon thereon;

aligning the position marker with a desired portion of the catheter so as to position the balloon; and bonding the balloon to the catheter.

2. The method of claim 1 further comprising the step of mounting the aligned stent on the balloon.

3. The method of claim 1 further comprising the steps of:

providing the medical balloon with a second reference marking so as to identify at least one portion of the medical balloon other than the middle portion.

* * * * *